United States Patent
Yang et al.

(10) Patent No.: US 9,921,137 B2
(45) Date of Patent: *Mar. 20, 2018

(54) RECIPROCATING MICROTOME DRIVE SYSTEM

(71) Applicant: Sakura Finetek U.S.A., Inc., Torrance, CA (US)

(72) Inventors: Hwai-Jyh Michael Yang, Cerritos, CA (US); Xuan S. Bui, Torrance, CA (US)

(73) Assignee: Sakura Finetek U.S.A., Inc., Torrance, CA (US)

(*) Notice: Subject to any disclaimer, the term of this patent is extended or adjusted under 35 U.S.C. 154(b) by 247 days.

This patent is subject to a terminal disclaimer.

(21) Appl. No.: 14/710,415

(22) Filed: May 12, 2015

(65) Prior Publication Data
US 2015/0241861 A1    Aug. 27, 2015

Related U.S. Application Data

(62) Division of application No. 13/333,942, filed on Dec. 21, 2011, now Pat. No. 9,032,854.

(51) Int. Cl.
*G01N 1/06* (2006.01)
*G05B 15/02* (2006.01)

(52) U.S. Cl.
CPC .............. *G01N 1/06* (2013.01); *G05B 15/02* (2013.01); *G01N 2001/065* (2013.01);
(Continued)

(58) Field of Classification Search
CPC ............... G01N 1/06; G01N 2001/065; A61B 10/0096; A61B 10/0275;
(Continued)

(56) References Cited

U.S. PATENT DOCUMENTS 2,155,523 A    4/1939    Bausch et al.
3,273,879 A    9/1966    Floren
(Continued)

FOREIGN PATENT DOCUMENTS

AU    2012200721    10/2012
CN    1268423    10/2000
(Continued)

OTHER PUBLICATIONS

Sakura Finetek U.S.A., Inc., Australian Examination Report dated Jun. 12, 2015, AU Appln. No. 2012355716, 5 pages.
(Continued)

*Primary Examiner* — Crystal J Barnes-Bullock
(74) *Attorney, Agent, or Firm* — Womble Bond Dickinson (US) LLP

(57) ABSTRACT

An apparatus having a sample sectioning device including a cutting mechanism that is operable to cut sections from a sample and a sample holder that is operable to hold the sample. The apparatus further includes a drive system coupled with the sample holder to drive movement of the sample holder and a reciprocating member coupled to the drive system to drive vertical movement of the drive system. The reciprocating member to move in a reciprocating manner within an angle of rotation of less than 180 degrees. A surface orientation sensor may further be provided that is operable to sense an orientation of a surface of the sample held by the sample holder.

8 Claims, 5 Drawing Sheets

(52) U.S. Cl.
CPC ............ *Y10S 83/9155* (2013.01); *Y10T 83/04* (2015.04); *Y10T 83/50* (2015.04); *Y10T 83/6475* (2015.04); *Y10T 83/654* (2015.04); *Y10T 83/6512* (2015.04); *Y10T 83/6563* (2015.04); *Y10T 83/6572* (2015.04)

(58) Field of Classification Search
CPC .......... A61B 2010/0225; B26D 7/0616; Y10T 83/04; Y10T 83/141; Y10T 83/525; Y10T 83/536; Y10T 83/538; Y10T 83/6499; Y10T 83/6512; Y10T 83/6563; Y10T 83/6572; Y10T 83/6577; Y10S 83/9155
See application file for complete search history.

(56) References Cited

U.S. PATENT DOCUMENTS

| | | |
|---|---|---|
| 3,926,085 A | 12/1975 | Shatzel |
| 3,962,937 A | 6/1976 | Miller |
| 4,150,593 A | 4/1979 | Butler |
| 4,517,870 A | 5/1985 | Kopp |
| 4,594,929 A | 6/1986 | Behme et al. |
| 5,065,657 A | 11/1991 | Pfeifer |
| 5,099,735 A | 3/1992 | Kempe et al. |
| D326,860 S | 6/1992 | Holbl |
| D326,921 S | 6/1992 | Holbl |
| D328,129 S | 7/1992 | Hoibl |
| 5,156,019 A | 10/1992 | McCormick |
| 5,161,446 A | 11/1992 | Holbl et al. |
| 5,226,335 A | 7/1993 | Sitte et al. |
| 5,255,585 A | 10/1993 | Gordon |
| 5,299,481 A | 4/1994 | Lihl et al. |
| D358,895 S | 5/1995 | Holbl |
| 5,461,953 A | 10/1995 | McCormick |
| 5,535,654 A | 7/1996 | Niesporek et al. |
| 5,609,083 A | 3/1997 | Persson |
| D383,548 S | 9/1997 | Hoelbl |
| 5,669,278 A | 9/1997 | Metzner |
| 5,671,648 A | 9/1997 | Dern |
| 5,673,905 A | 10/1997 | Kiene |
| 5,678,465 A | 10/1997 | Krumdieck |
| 5,695,942 A | 12/1997 | Farmilo et al. |
| 5,711,200 A | 1/1998 | Thiem |
| 5,740,708 A | 4/1998 | Tabone |
| 5,782,572 A | 7/1998 | Thiem |
| 5,817,032 A | 10/1998 | Williamson, IV et al. |
| 5,881,626 A | 3/1999 | Kiene et al. |
| 5,906,148 A | 5/1999 | Aihara et al. |
| 5,964,138 A | 10/1999 | Metzner et al. |
| 5,965,454 A | 10/1999 | Farmilo et al. |
| 5,974,811 A | 11/1999 | Held et al. |
| 6,041,686 A | 3/2000 | Lihl et al. |
| 6,058,788 A | 5/2000 | Thiem et al. |
| 6,058,824 A | 5/2000 | Neymeyr |
| 6,080,365 A | 6/2000 | Thiem et al. |
| 6,178,757 B1 | 1/2001 | Sitte et al. |
| 6,209,437 B1 | 4/2001 | Izvoztchikov et al. |
| 6,231,037 B1 | 5/2001 | Metzner |
| 6,253,653 B1 | 7/2001 | Walter et al. |
| 6,349,264 B1 | 2/2002 | Rhett et al. |
| 6,387,653 B1 | 5/2002 | Voneiff et al. |
| 6,568,307 B1 | 5/2003 | Gunther et al. |
| 6,598,507 B1 | 7/2003 | Gunther et al. |
| 6,634,268 B1 | 10/2003 | Guenther et al. |
| 6,635,225 B1 | 10/2003 | Thiem et al. |
| 6,637,737 B1 | 10/2003 | Beecherl et al. |
| 6,644,162 B1 | 11/2003 | Temple et al. |
| 6,651,538 B2 | 11/2003 | Tamura et al. |
| 6,705,187 B2 | 3/2004 | Konrad |
| 6,715,870 B2 | 4/2004 | Kiene et al. |
| 6,763,972 B2 | 7/2004 | Graupner |
| 6,766,593 B2 | 7/2004 | Laudat et al. |
| 6,827,900 B2 | 12/2004 | Thiem et al. |
| 6,860,113 B2 | 3/2005 | Goll |
| 7,044,038 B2 | 5/2006 | Hess |
| 7,080,583 B2 | 7/2006 | Lihl et al. |
| 7,104,666 B2 | 9/2006 | Lihl et al. |
| 7,111,535 B2 | 9/2006 | Hess |
| 7,168,694 B2 | 1/2007 | Bui et al. |
| 7,168,901 B2 | 1/2007 | Ranner |
| 7,240,497 B2 | 7/2007 | Dorenkamp et al. |
| 7,273,000 B2 | 9/2007 | Thiem et al. |
| 7,287,388 B2 | 10/2007 | Dorenkamp et al. |
| 7,313,993 B2 | 1/2008 | Foerderer |
| 7,357,384 B2 | 4/2008 | Thiem |
| 7,371,346 B2 | 5/2008 | Windeyer et al. |
| 7,374,907 B1 | 5/2008 | Voneiff et al. |
| 7,600,457 B2 | 10/2009 | Voneiff et al. |
| 7,673,546 B2 | 3/2010 | Dorenkamp et al. |
| 7,854,707 B2 | 12/2010 | Hibner et al. |
| 7,900,545 B2 | 3/2011 | Schneider |
| 7,938,379 B2 | 5/2011 | Baten |
| 7,966,917 B2 | 6/2011 | Schneider |
| 8,001,876 B1 | 8/2011 | Tabb et al. |
| 8,001,878 B2 | 8/2011 | Lang et al. |
| 8,056,456 B2 | 11/2011 | Walter |
| 8,074,545 B1 | 12/2011 | Tabb et al. |
| 8,088,330 B1 | 1/2012 | Nakajima et al. |
| 8,256,332 B2 | 9/2012 | Walter |
| 8,353,232 B2 | 1/2013 | Walter et al. |
| 8,555,758 B2 | 10/2013 | Ranner et al. |
| 8,869,666 B2 * | 10/2014 | Yang ........................ G01N 1/06 83/360 |
| 9,017,147 B2 * | 4/2015 | Vindler ................ B23D 45/003 451/121 |
| 9,347,857 B2 * | 5/2016 | Yang ........................ G01N 1/06 |
| 2003/0022271 A1 | 1/2003 | Voneiff et al. |
| 2003/0101858 A1 | 6/2003 | Tamura et al. |
| 2005/0161873 A1 | 7/2005 | Bui |
| 2005/0235542 A1 | 10/2005 | Metzner et al. |
| 2006/0179992 A1 | 8/2006 | Kermani |
| 2007/0091428 A1 | 4/2007 | Wilson |
| 2007/0180965 A1 | 8/2007 | Ito et al. |
| 2007/0193990 A1 | 8/2007 | Richerzhagen |
| 2008/0072722 A1 | 3/2008 | Tanki et al. |
| 2008/0113440 A1 | 5/2008 | Gurney et al. |
| 2008/0115640 A1 | 5/2008 | Ranner |
| 2009/0084235 A1 | 4/2009 | Kata et al. |
| 2009/0241751 A1 | 10/2009 | Walter |
| 2010/0000390 A1 | 1/2010 | Fank |
| 2010/0003907 A1 | 1/2010 | Hirayama et al. |
| 2010/0064867 A1 | 3/2010 | Schmitt |
| 2010/0076473 A1 | 3/2010 | Tawfik et al. |
| 2011/0283850 A1 | 11/2011 | Tabb et al. |
| 2012/0240737 A1 | 9/2012 | Yang et al. |
| 2013/0186248 A1 | 7/2013 | Heid |
| 2014/0026728 A1 | 1/2014 | Walter |
| 2014/0090531 A1 | 4/2014 | Schmitt |
| 2014/0318342 A1 | 10/2014 | Koegel et al. |
| 2014/0335554 A1 * | 11/2014 | Larson ..................... G01N 1/08 435/29 |

FOREIGN PATENT DOCUMENTS

| | | |
|---|---|---|
| CN | 1201140 C | 5/2005 |
| CN | 101000335 A * | 7/2007 |
| CN | 201000346 Y * | 1/2008 |
| EP | 1566620 | 8/2005 |
| EP | 2503315 | 9/2012 |
| JP | 05256745 | 10/1993 |
| JP | 10504103 | 4/1998 |
| JP | 2000283899 | 10/2000 |
| JP | 2000283900 | 10/2000 |
| JP | 2002539424 | 11/2002 |
| JP | 2005208049 | 8/2005 |
| JP | 2008134127 | 6/2008 |
| JP | 2010066006 | 3/2010 |
| WO | WO-9115746 | 10/1991 |
| WO | WO-0054020 | 9/2000 |

(56) References Cited

FOREIGN PATENT DOCUMENTS

| WO | WO-2007094206 | 8/2007 |
| WO | WO-2010081497 | 7/2010 |

OTHER PUBLICATIONS

Sakura Finetek U.S.A., Inc., Chinese Office Action dated Jul. 16, 2015, Chinese Appln. No. 2012800624381, with English-language translation, 13 pages.

Sakura Finetek U.S.A., Inc., European Office Action dated Jun. 17, 2015 for EP Appln. No. 12159609.2, 7 pages.

Sakura Finetek U.S.A., Inc., Final Office Action for U.S. Appl. No. 14/502,915, (dated Sep. 23, 2015).

Sakura Finetek U.S.A., Inc., Japanese Office Action for JP Appln. No. 201261804 with English translation, (dated Sep. 29, 2015), 31 pages.

Sakura Finetek U.S.A., Inc., Australian Examination Report for AU Appln. No. 2012355716, (dated Oct. 26, 2015), 3 pages.

Sakura Finetek U.S.A., Inc., Chinese Office Action for Chinese Appln. No. 201210071976.9, with English-language translation, (dated Nov. 24, 2015), 36 pages.

Sakura Finetek U.S.A., Inc., EP Office Action for EP Appln. No. 12814045.6, (dated Nov. 16, 2015), 6 pages.

Sakura Finetek U.S.A., Inc., Australian Examination Report, AU Appln. No. 2012355716, (dated Jan. 19, 2016), 3 pages.

Sakura Finetek U.S.A., Inc., Japanese Office Action for JP Appln. No. 201261804 with English translation, (dated Feb. 9, 2016), 5 pages.

Sakura Finetek U.S.A., Inc., International Search Report and Written Opinion dated Jun. 21, 2013 for PCT/US2012/068747.

Sakura Finetek U.S.A., Inc., International Preliminary Report on Patentability dated Jul. 3, 2014 for PCT/US2012/068747.

Sakura Finetek U.S.A., Inc., et al., European search report dated Dec. 3, 2012 for EP Appln. No. 12159609.2.

Sakura Finetek USA, Inc., European Office Action dated Oct. 29, 2014 for EP Appln. No. 12159609.2, 8 pages.

Sakura Finetek U.S.A., Inc., Chinese Office Action dated Apr. 28, 2015, Chinese Appln. No. 201210071976.9, with English-language translation.

Sakura Finetek U.S.A., Inc., Japanese Office Action dated May 7, 2015, JP Appln. No. 2014-549101, with English-language translation.

Sakura Finetek U.S.A., Inc., Notice of Allowance for Chinese Appln. No. 201280062438.1, dated Sep. 5, 2016.

Sakura Finetek U.S.A., Inc., Notice of Allowance for Canadian Appln. No. 2,858,196 dated Dec. 5, 2016.

Sakura Finetek U.S.A., Inc., Chinese Office Action, Chinese Appln. No. 2012800624381, with English-language translation, (dated Mar. 15, 2016), 9 pages.

Sakura Finetek USA Inc., EP Office Action for EP Appln. No. 12814045.6, (dated Jul. 13, 2016).

Sakura Finetek U.S.A., Inc., Japanese Notice of Rejection dated Jun. 26, 2017, JP Application No. 2016-123622.

Sakura Finetek U.S.A., Inc., Examiner's Report dated Sep. 20, 2017, Canadian Application No. 2,858,196.

Sakura Finetek U.S.A., Inc., Extended European Search Report dated Sep. 28, 2017, EP Application No. 17173912.1.

\* cited by examiner

US 9,921,137 B2

RECIPROCATING MICROTOME DRIVE SYSTEM

CROSS-REFERENCE TO RELATED APPLICATION

This application is a divisional co-pending U.S. patent application Ser. No. 13/333,942, filed Dec. 21, 2011 and incorporated herein by reference.

BACKGROUND

Field

Embodiments of the invention relate to microtomes or other tissue sample sectioning devices to produce sections of samples, specifically some embodiments relate to microtomes or other tissue sample sectioning devices that have a reciprocating drive system.

Background

Histology is a science or discipline associated with the processing of tissue for examination or analysis. The examination or analysis may be of the cellular morphology, chemical composition, tissue structure or composition, or other tissue characteristics.

In histology, a sample of tissue may be prepared for sectioning by a microtome or other sample sectioning device. Commonly, the tissue may be dried or dehydrated by removing most or almost all of the water from the tissue, for example by exposing the tissue to one or more dehydrating agents. After drying the tissue, clearing of the dehydrating agents may optionally be performed, and then an embedding agent (e.g., wax with added plasticizers) may be introduced or infiltrated into the dried tissue. The removal of the water and the infiltration of the embedding agent may aid in sectioning the tissue into thin sections with the microtome.

Embedding may then be performed on the tissue. During embedding, the tissue that has been dried and infiltrated with the embedding agent may be embedded in a block or other mass of wax, various polymers, or another embedding medium. Representatively, the dried and wax-infiltrated tissue may be placed in a mold and/or cassette, melted wax may be dispensed over the tissue until the mold has been filled with the wax, and then the wax may be cooled and hardened. Embedding the tissue in the block of wax may help to provide additional support during cutting or sectioning of the tissue with a microtome.

The microtome may be used to cut thin slices or sections of the sample of tissue. Various different types of microtomes are known in the arts. Representative types include, for example, sled, rotary, vibrating, saw, and laser microtomes. The microtomes may be manual or automated. Automated microtomes may include motorized systems or drive systems to drive or automate a cutting movement between the sample from which the sections are to be cut and a cutting mechanism used to cut the sections. It is to be appreciated that microtomes may also be used for other purposes besides just histology, and that microtomes may be used on other types of samples besides just embedded tissue.

BRIEF DESCRIPTION OF THE DRAWINGS

The invention may best be understood by referring to the following description and accompanying drawings that are used to illustrate embodiments of the invention. In the drawings.

DETAILED DESCRIPTION

In the following description, numerous specific details, such as particular microtomes, particular cutting drive systems, particular sensors, particular sensing mechanisms, particular surface orientation measurement and/or adjustment processes, and the like, are set forth. However, it is understood that embodiments of the invention may be practiced without these specific details. In other instances, well-known mechanical components, circuits, structures and techniques have not been shown in detail in order not to obscure the understanding of this description.

Figure 1:
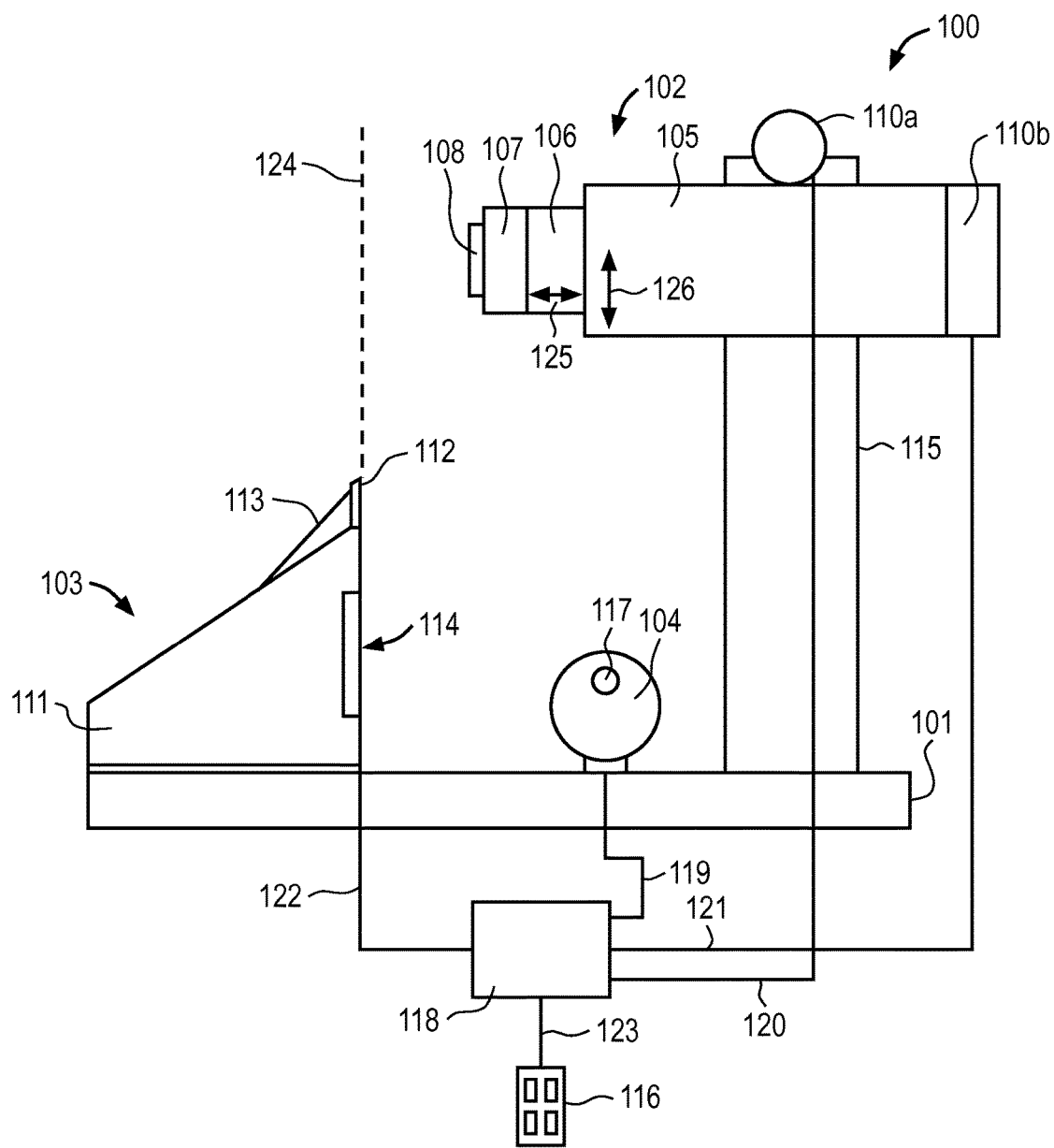
FIG. 1 illustrates a schematic side view of an embodiment of a sample sectioning device.

FIG. 1 illustrates a schematic side view of an embodiment of a sample sectioning device such as a microtome. In this embodiment, microtome 100 includes base member 101 having feed drive system or cutting drive system 102, mounting member 103 and handwheel 104 attached thereto. Feed drive system 102 is supported above base member 101 by support member 115. Feed drive system 102 includes vertical drive member 105, horizontal drive member 106 and sample holder 107 operable to hold sample 108. Sample 108 may include a piece of tissue that is to be sectioned, for example, a piece of tissue embedded in a paraffin block. The cutting drive system or feed drive system 102 is operable to drive movement of sample 108 held by the sample holder 107. Motor 110a of feed drive system 102 is mechanically coupled to vertical drive member 105 and, operable to drive vertical movement of vertical drive member 105 in a direction of vertical double arrow 126. Another motor 110b of feed drive system 102 may also be mechanically coupled to horizontal drive member 106 to drive horizontal movement of horizontal drive member 106 in a direction of horizontal double arrow 125. It should be noted that terms such as "horizontal", "vertical", "top", "bottom", "upper", "lower", and the like, are used herein to facilitate the description of the illustrated device according to the orientation shown in FIG. 1. It is possible for other devices to replace horizontal movements with vertical movements, etc.

Referring again to the embodiment shown in FIG. 1, mounting member 103 includes mounting base 111 which provides a mounting surface for cutting member or mechanism 112. Cutting member or mechanism 112 may be, for example, a blade or knife of various types of materials mounted to mounting member 103, or other types of cutting mechanisms suitable for microtomes. Section receiving member 113 is positioned along one side of cutting member 112. Section receiving member 113 is dimensioned to receive a section cut from sample 108 by cutting member or blade 112. In this aspect, section receiving member 113 may have an inclined surface extending from a cutting edge of blade 112 to the surface of mounting member 103. As cutting member or blade 112 slices through sample 108, the section cut from sample 108 is separated from sample 108 and extends along section receiving member 113.

As shown, in some embodiments, microtome 100 includes a surface orientation sensor assembly 114. Surface orientation sensor assembly 114 is operable to sense or measure an orientation or angle of a surface of sample 108. The orientation or angle of the surface of sample 108 may be sensed or determined in various ways. In some embodiments, the surface of sample 108 may contact sensor assembly 114, and one or more movable portions of sensor assembly 114 may conform to an orientation of the surface of sample 108. The movement of the one or more movable portions of sensor assembly may allow microtome 100 to autonomously sense or determine the orientation of the surface of sample 108. Optical and other sensing mechanisms are also suitable.

The sensed orientation may be used to adjust or align the surface of sample 108 so that it is parallel, substantially parallel, or at least more parallel with cutting member or mechanism 112 and/or cutting plane 124 associated with cutting member or mechanism 112 than it was prior to sensing. It is advantageous that the surface of sample 108 be sufficiently aligned parallel with cutting member 112 and/or cutting plane 124 so that the sample sections cut by microtome 100 are sufficiently evenly cut. In some embodiments, microtome 100 may optionally be capable of autonomously adjusting or aligning the orientation of the surface of sample 108 parallel, sufficiently parallel, or at least more parallel, with cutting member 112 and/or cutting plane 124. Microtome 100 may have logic to autonomously sense and/or adjust an orientation of the surface of the sample relative to a cutting plane and/or cutting mechanism based on the sensed orientation. Advantageously, this may help to improve alignment accuracy and/or relieve an operator from performing the adjustment manually. Alternatively, the adjustment may be performed manually, if desired. An embodiment of a method of sectioning may include microtome 100 autonomously sensing an orientation of a surface of sample 108 using sensor assembly 114, an operator manually or microtome 100 autonomously adjusting the orientation of the surface of sample 108, and microtome 100 taking a section of sample 108 after such adjustment.

In the illustrated embodiment, sensor assembly 114 may be in a fixed positioned approximately vertically below cutting member or mechanism 112 and/or cutting plane 124. One potential advantage to positioning sensor assembly 114 vertically below cutting member 112 is that sample 108 may not need to traverse a substantial distance in the horizontal direction of arrow 125 to reach cutting member 112 and/or cutting plane 124. This may help to reduce the amount of time for sample 108 to move horizontally to cutting member 112. In one embodiment, movement in the direction of arrow 125 (horizontal movement) should be fine as a thickness of a sample section will be based in part on this translation or movement. It is appreciated that a microtome such as microtome 100 may be used to cut sample sections having a thickness in the range of 0.5 to 50 microns. Such relatively small thicknesses require translation in the direction of arrow 125 to be capable of translation within this pitch (e.g., translation of ±0.5 micron in a direction of arrow 125). It is appreciated that significant distance to be translated in the direction of arrow 125 (e.g. ½ inch to 1 inch) will be time consuming. In addition, processing time can be improved by allowing vertical movement of vertical drive member 105 to be relatively faster than horizontal movement of horizontal drive member 106. This may help to speed up the time to sense surface orientations and adjust the surface orientations.

In other embodiments, sensor assembly 114 may be movably coupled to mounting base 111 at a position between feed drive system 102 and mounting member 103, although this is not required. In this embodiment, mounting base 111 provides a support surface for sensor assembly 114 and is dimensioned and coupled to accommodate sliding of sensor assembly 114 vertically. During operation, sensor assembly 114 is operable to slide along mounting base 111 in an upward vertical direction toward feed drive system 102, and vertical drive member 105 is operable to cause feed drive system 102 to move in a downward vertical direction toward sensor assembly 114. Once sample 108 is sufficiently vertically aligned with sensor assembly 114, horizontal drive member 106 is operable to cause feed drive system 102 to move in a horizontal direction toward sensor assembly 114 in the direction of horizontal arrow 125 so that a surface of sample 108 is appropriately positioned relative to sensor assembly 114 to allow for surface orientation measurement. Once the orientation of the surface of sample 108 is determined, and realigned if appropriate, sensor assembly 114 is operable to retract in a vertical downward direction as viewed (e.g., to a retracted position away from the movement between the sample held by the sample holder and the cutting mechanism.)

Referring again to FIG. 1, operation of feed drive system 102 may be controlled using handwheel 104 and/or control device 116. Handwheel 104 may include handle or other pulse generating device 117 to lock the handwheel 104. Rotation of handwheel 104 may be operable to cause vertical drive member 105 to move in a vertical direction shown by vertical double arrow 126 to facilitate slicing of sample 108. In some embodiments, handwheel 104 may be a decoupled handwheel, which is not mechanically coupled to feed drive system 102. Rather, decoupled handwheel 104 may be electrically connected to an encoder (not shown) and control circuit 118 via control line 119. The rotation of decoupled handwheel 104 may cause the encoder to deliver an electrical signal to control circuit 118. Control circuit 118 is connected to motor 110a via control lines 120 and is operable to control movement of vertical drive member 105 according to the electrical signal from the encoder. Control circuit 118 is also connected to motor 110b via control line 121 to control movement of horizontal drive member 106 and is connected to sensor assembly 114 via control line 122.

In addition to signals from the encoder, signals from control device 116 may be transmitted to control circuit 118 to control or facilitate operation of sensor assembly 114, handwheel 104 and motor 110a, 110b. In some embodiments, control device 116 may be, for example, a keyboard, a capacitive sensor touch pad, or other user or data input device. In some embodiments, signals are transmitted between control device 116 and control circuit 118 via control line 123. In other embodiments, control device 116 is a wireless control device that is operable to wirelessly transmit signals to control circuit 118 and control line 123 is omitted.

Figure 2A:
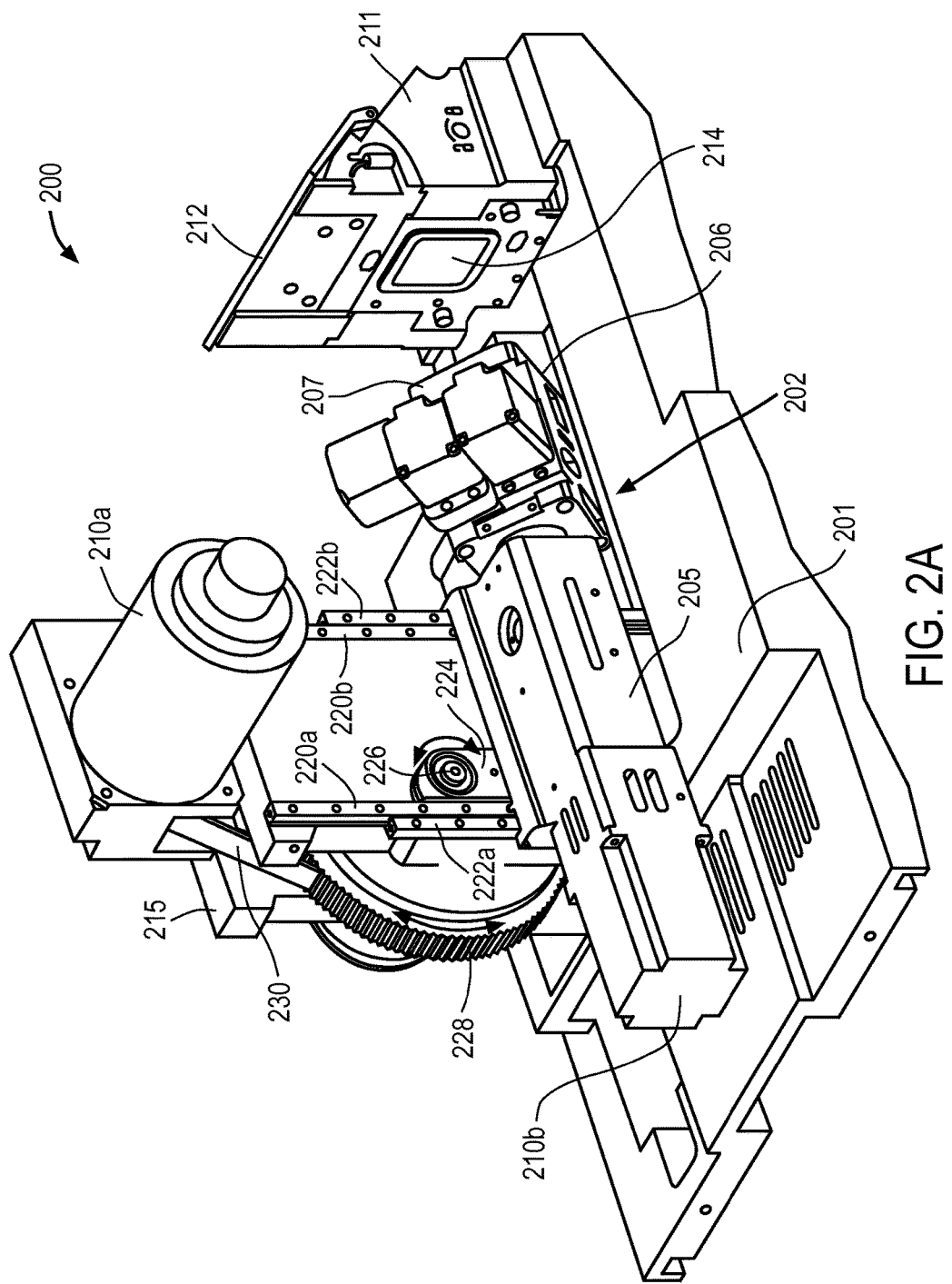
FIG. 2A illustrates a perspective view of a sample sectioning device in a lowered position for sample sensing.
Figure 2B:
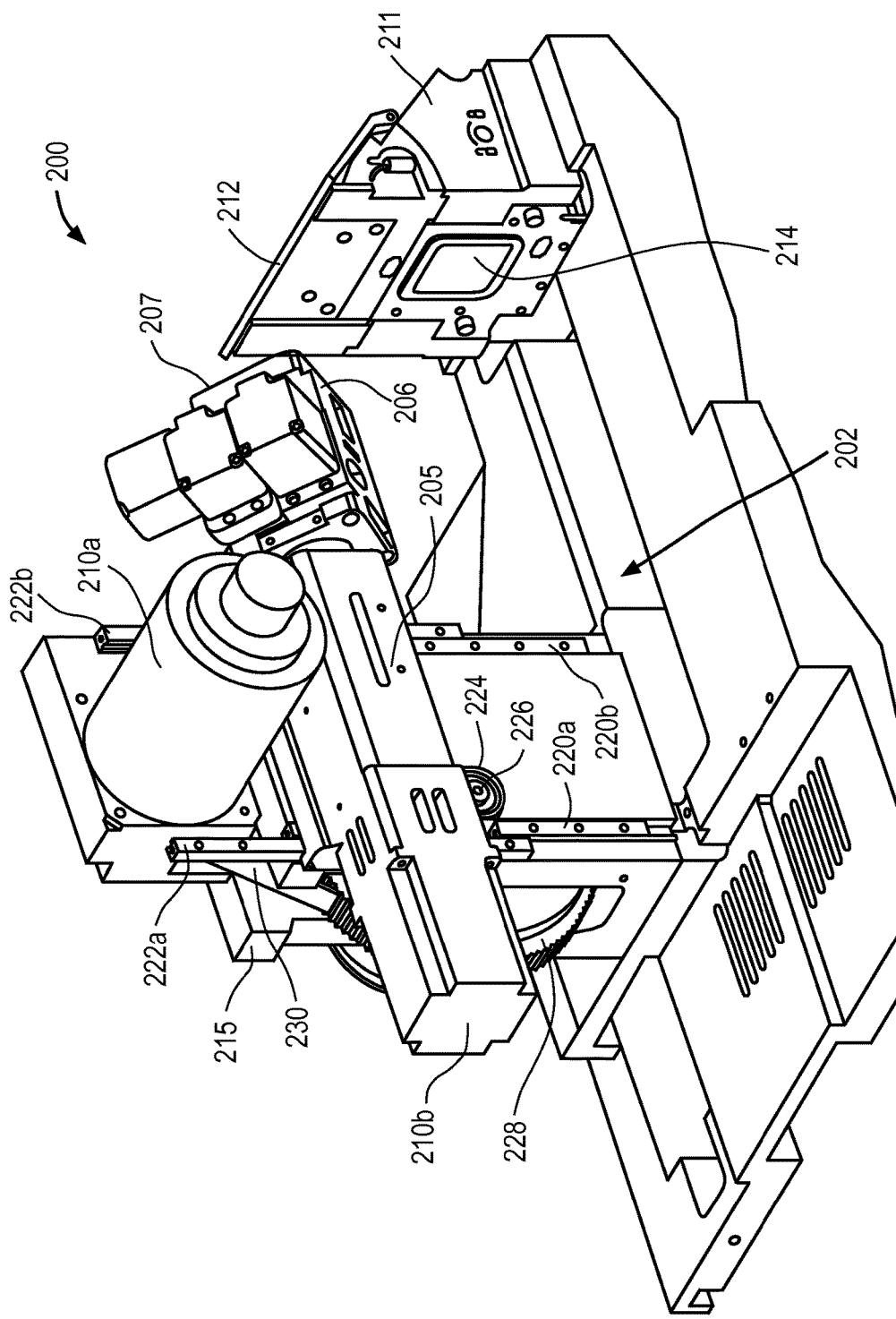
FIG. 2B illustrates a perspective view of a sample sectioning device in a raised position for sample sectioning.

FIG. 2A and FIG. 2B illustrate one embodiment of a sample sectioning device having a reciprocating member for driving a vertical movement of the feed drive system. In FIG. 2A, the drive member is in a lowered position suitable for sensing an orientation of the sample. In FIG. 2B the drive member is in a raised position suitable for sample sectioning.

Returning to FIG. 2A, similar to FIG. 1, the sample sectioning device may be a microtome 200 including sensor assembly 214 and cutting member 212 vertically aligned and attached to mounting base 211. Feed drive system 202 may be supported above base member 201 by support member 215. Feed drive system 202 may include vertical drive member 205, horizontal drive member 206 and sample holder 207 operable to hold a sample (not shown). From this view, reciprocating arm member 224 for driving vertical movement of feed drive system 202 can be seen. Reciprocating arm member 224 is fixedly attached at one end to pin member 226, which extends from rotating disk member 228, and rotatably attached at the opposite end to vertical drive member 205 of feed drive system 202. Rotation of rotating disk member 228 in a reciprocating manner (i.e. alternatively forward and backward) causes pin member 226 to rotate in the same direction. The reciprocal motion of pin member 226 causes the end of reciprocating arm member 224 attached to vertical drive member 205 to move in a reciprocating manner, meaning that it also moves alternately forward and backward. In some embodiments, reciprocating arm member 224 reciprocates within a 180 degree angle of rotation (e.g. moves upward 90 degrees and downward 90 degrees). Movement of reciprocating arm member 224 in this manner in turn drives vertical movement of vertical drive member 205.

FIG. 2A illustrates an embodiment where reciprocating arm member 224 is rotated from a first vertical position (a 0 degrees position) illustrated by FIG. 2B to a second vertical position (a rotation of 180 degrees with respect to the first position). At the second vertical position, feed drive system 202, and in turn sample holder 207, is aligned with sensor assembly 214. Once at this position, horizontal drive member 206 may move laterally (horizontally viewed) to cause a sample attached to sample holder 207 to contact sensor assembly 214 so that an orientation of the sample may be determined.

Once the orientation of the sample is determined, and corrected if necessary, reciprocating arm member 224 rotates back to the first vertical position (the 0 degrees position) illustrated in FIG. 2B to begin a sample cutting operation. Cutting of the sample may be achieved by rotating reciprocating arm member 224, and in turn moving sample holder 207 attached to vertical drive member 205 in a vertical direction, along an approximately 90 degree angle of rotation. For example, when reciprocating arm member 224 is at the first vertical position, vertical drive member 205, and in turn the sample, is positioned above cutting member 212. Rotation of reciprocating arm member 224 approximately 90 degrees to a substantially horizontal position causes the sample to move in a downward direction across cutting member 212 resulting in removal of a section from the sample. Reciprocating arm member 224 may then be rotated 90 degrees from the substantially horizontal position back to the first vertical position to complete the cutting stroke. Reciprocating arm member 224 may continue to reciprocate within this 90 degree angle of rotation until a sufficient number of sample sections are obtained. The sample position may be adjusted in a horizontal direction by horizontal drive member 206 prior to or after each downward slicing movement to achieve the desired sample section width.

Although sample sectioning by moving reciprocating arm member 224 along a 90 degree angle of rotation is disclosed in one embodiment, it is contemplated that the angle of rotation may vary and is dictated by the size of the sample. For example, where the sample is a 30 mm by 30 mm block, a single cutting stroke or sectioning cycle requires movement of the sample approximately 35 mm in a downward vertical direction to slice a section from the sample and then movement of the sample in an upward vertical direction approximately 35 mm back to the start position. Thus, in the case of a 30 mm sample, a single cutting stroke requires vertical drive member 205 to move the sample a total distance of approximately 70 mm. Movement of reciprocating arm member 224 from the first vertical position to the horizontal position and then back to the first vertical position along the 90 degree angle of orientation translates to a 70 mm cutting stroke. Where the sample is smaller, however, a shorter cutting stroke can be used to obtain a sample section. Representatively, where the sample is a 15 mm by 15 mm block, a single cutting stroke requires movement of the sample approximately 22 mm in a downward vertical direction to slice a section from the sample and then movement of the sample in an upward vertical direction approximately 22 mm back to the start position. In this case, a single cutting stroke requires a total vertical movement of approximately 44 mm. This shortened cutting stroke may be achieved by rotating reciprocating arm member 224 along an angle of rotation which is less than 90 degrees, for example between 0 and 60 degrees, or 0 and 45 degrees. In any case, it is recognized that since a single cutting stroke is driven by the reciprocating motion of reciprocating arm member 224, as opposed to a full 360 degree rotation, the time required to complete each cutting stroke is reduced resulting in a faster slicing operation.

In addition, the time required to complete each cutting stroke may be reduced by modifying the speed of reciprocating arm member 224 throughout the sectioning cycle. For example, in some embodiments, a relatively faster speed of movement of reciprocating arm member 224, and in turn, feed drive system 202 and/or a sample may be used during one or more non-sectioning portions of a sectioning cycle or stroke (e.g., where cutting or sectioning of a sample is not performed), whereas a relatively slower speed of movement may be used during a sectioning portion of the sectioning cycle or stroke (e.g., where cutting or sectioning of the sample is performed). Using a relatively slower speed of movement of the feed drive system and/or sample during cutting or sectioning of the sample tends to provide higher quality sections and/or more consistent sections, whereas performing one or more other non-sectioning portions of the sectioning cycle more rapidly may help to improve the overall speed of the sectioning cycle and/or may allow more sections to be produced in a given amount of time.

Representatively, microtome 200 may include logic to allow reciprocating arm member 224 to move at one speed while the sample is being cut and a second, faster speed before or after cutting of the sample. For example, the logic may allow for a sectioning length to be specified (e.g. 35 mm), reciprocating arm member 224 may move the sample at a relatively slower speed during the specified sectioning length and at a relatively faster speed just before and just after movement during the specified sectioning length (e.g. during movement of reciprocating arm member 224 from the horizontal position back to the first vertical position). The length may be selected from among a plurality of predetermined lengths corresponding to different types of cassettes having different dimensions. In one example embodiment, microtome 200 may be operable to allow an operator to specify or indicate a sectioning length. The specification or indication of the sectioning length may be done in different ways, such as, for example, by specifying a length, selecting a length from among a plurality of predetermined lengths, specifying a type of cassette, selecting a type of cassette from among a plurality of different types of cassettes, etc. For example, when a user is ready to produce sections from a particular type of cassette, the user may make a selection of the particular type of cassette using a control device (e.g., control device 116 in FIG. 1), and the microtome may already be preprogrammed with a predetermined sectioning length corresponding to that particular type of cassette. During sectioning, the microtome may use a relatively slower speed of movement of the feed drive system and/or the sample over the specified sectioning length and may use relatively faster speeds of movement over one or more or substantially all other portions of the sectioning cycle. For example, immediately or just before and immediately or just after the cutting of the sample over the specified sectioning length the relatively faster speeds may be used.

In addition, microtome may include logic to initially autonomously remove a given or predetermined portion of a sample (e.g., sample 108 in FIG. 1). For example, the portion may include a given or predetermined thickness of paraffin, embedding material, cassette material, or other non-tissue material overlying or concealing the actual tissue material from which a section is desired to be taken (e.g., disposed between a cutting surface of the tissue material and the foremost external surface of the sample which would contact a sensing plate). By way of example, a sample may include a piece of tissue placed on a bottom of a cassette and the cassette and the tissue sample embedded in a block of embedding material. In the case of various cassettes manufactured by Sakura Finetek USA, Inc., of Torrance, Calif., the cassettes may include a Paraform® brand cassette material that has sectioning characteristics similar to that of paraffin and sectioning may be performed through the Paraform® brand cassette material of the cassette bottom. Once the actual tissue of the sample is exposed, a sectioning cycle to obtain slices or sections of the tissue may be commenced (e.g., the operator may press a section button or otherwise cause the microtome to take a section from the now exposed cutting surface of the tissue sample. In some embodiments, microtome 200 may include logic to allow reciprocating arm member 224 to move at a faster speed to remove these initial sections and then a relatively slower speed once sectioning of the tissue is commenced.

It is further contemplated that logic may be provided to increase the speed of movement of reciprocating arm member 224 between the second vertical position (for sensing the sample orientation) and first vertical position (for cutting the sample) so that an overall speed of the processing operation may be reduced. For example, in some embodiments, feed drive system 202 must be lowered from the raised position illustrated in FIG. 2B approximately 134 mm to align the sample with sensor assembly 214. In this aspect, the logic may allow for a sensing length to be specified (e.g. 134 mm) and reciprocating arm member 224 may move faster along the specified sensing length in order to reduce processing time.

Movement of rotating disk member 228 may be driven by motor 210a. For example, in one embodiment, motor belt 230 is looped around an outer perimeter of rotating disk member 228. Motor 210a pulls motor belt 230 causing rotating disk member 228 to rotate in a clockwise direction (e.g. lowering vertical drive member 205) or counter-clockwise direction (e.g. raising vertical drive member 205). Motor 210a may pull motor belt 230 in alternating directions to cause reciprocating movement of reciprocating arm member 224. In addition, motor 210a may move motor belt 230 at different speeds during a sectioning operation to change the speed in which various operations (e.g. sectioning steps and non-sectioning steps) are performed throughout the sectioning cycle and/or to maintain a linear speed throughout the sectioning operation. Although a belt and rotating disk type system is disclosed, it is contemplated that any type of driving mechanism may be used to cause reciprocating arm member 224 to move in a reciprocating motion.

Horizontal movement of feed drive system 202 may be driven by motor 210b as previously discussed.

To facilitate alignment and vertical movement of vertical drive member 205, feed drive system 202 may be slidably attached to support member 215 by inner slide rails 220a, 220b and outer slide rails 222a, 222b. Inner slide rails 220a, 220b may have a lip that fits within grooves formed by outer slide rails 222a, 222b so that inner slide rails 220a, 220b can slide with respect to outer slide rails 222a, 222b. Outer slide rails 222a, 222b may be fixedly attached to support member 215 while inner slide rails 220a, 220b are fixedly attached to vertical drive member 205. Alternatively, outer slider rails 222a, 222b may be fixedly attached to vertical drive member 205 while inner slide rails 220a, 220b may be fixedly attached to support member 215. In either case, when vertical drive member 205 is moved by reciprocating arm member 224, outer slide rails 222a, 222b slide with respect to inner slide rails 220a, 220b so that vertical drive member 205 moves in a vertical direction.

Figure 3:
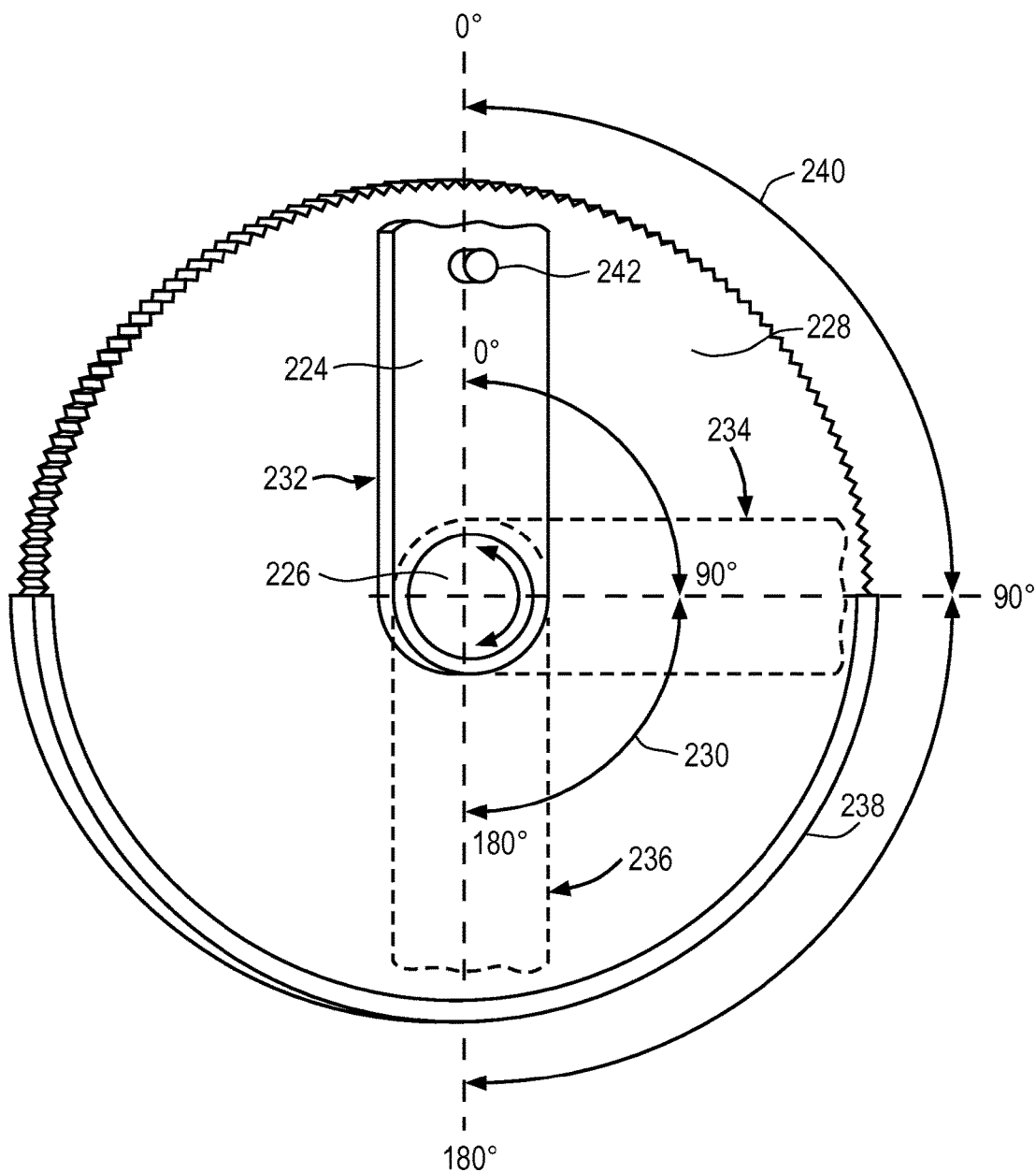
FIG. 3 illustrates a perspective view of a reciprocating member of a sample sectioning device.

FIG. 3 illustrates a perspective view of reciprocating arm member 224 and rotating disk member 228 described in reference to FIGS. 2A and 2B. From this view, it can be seen that reciprocating arm member 224 is attached to rotating disk member 228 by pin 226. Reciprocating arm member 224 may have any size and shape suitable for driving reciprocal movement of the attached drive system (not shown) between the slicing and sensing positions. For example, where a distance between the raised position of the drive member (see FIG. 2B cutting position) and lowered position of the drive member (FIG. 2A sensing position) is approximately 134 mm, reciprocating arm member 224 may have a length of approximately 67 mm such that reciprocating arm member 224 can move the drive member a total distance of approximately 134 mm.

Rotation of rotating disk member 228 along a 180 degree angle of rotation 240 rotates pin 226, which in turn drives rotation of reciprocating arm member 224 along a 180 degree angle of rotation 230. At the first vertical position 232, reciprocating arm member 224 is at a 0 degree angle of rotation. Rotation of rotating disk member 228 90 degrees clockwise, causes reciprocating arm member 224 to rotate 90 degrees to the horizontal position 234. Reciprocating arm member 224 may be rotated in a reciprocating manner (i.e. forward and backward) between first vertical position 232 and horizontal position 234 during a cutting cycle or stroke.

Rotation of rotating disk member 228 180 degrees from the 0 degree position, causes reciprocating arm member 224 to rotate 180 degrees to the second vertical position 236. At this position, the vertical drive member is aligned with the sensor assembly so that an orientation of the sample can be determined. It is contemplated that although reciprocating arm member 224 is illustrated at three positions (i.e. first vertical position 232, horizontal position 234 and second vertical position 236) other positions may be suitable for aligning the sample with the sectioning member or sensing assembly during a sensing or sensing operation, respectively. For example, sectioning of the sample may occur by moving reciprocating arm member 224 in a reciprocating manner along an angle of rotation less than 90 degrees, for example between 0 degrees and 60 degrees, or between 0 degrees and 45 degrees, depending upon a size of the sample block.

Rotating disk member 228 may further include counterweight 238 to counterbalance feed drive system 202 attached to rotating disk member 228. Counterweight 238 may, however, be optional and therefor omitted in some embodiments.

Figure 4:
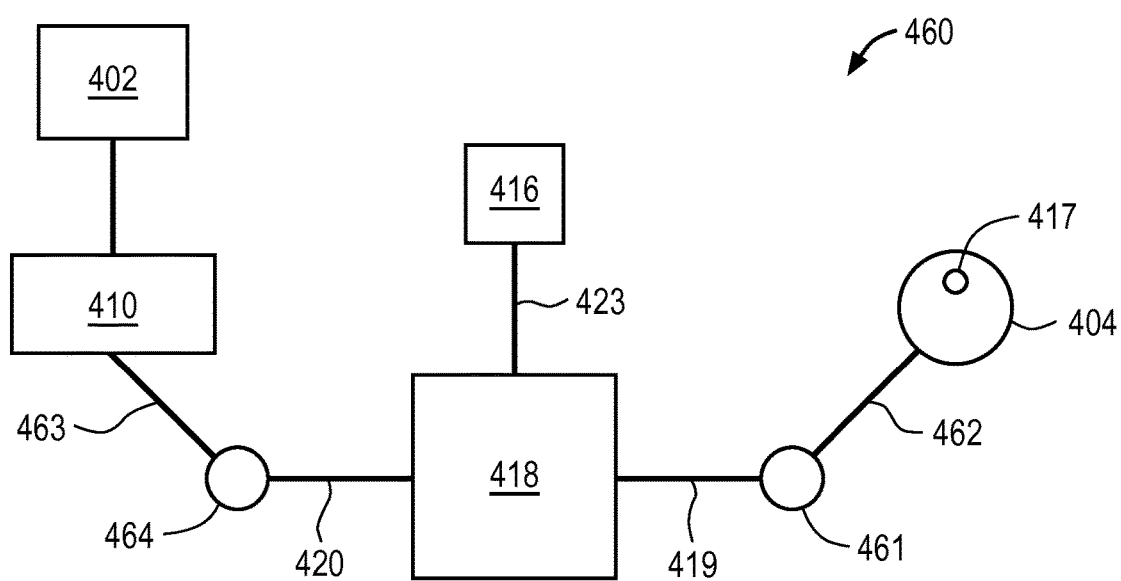
FIG. 4 illustrates an embodiment of a control system for controlling an operation of a sample sectioning device including a handwheel and control device.

The slicing operation may proceed automatically or manually through user interaction with the system. FIG. 4 illustrates an embodiment of a control system for controlling an operation of the microtome including a handwheel and control device. Control system 460 may include handwheel 404 and control device 416. Handwheel 404 may include handle or other pulse generating device 417 to lock handwheel 404. In some embodiments, handwheel 404 is coupled to motor 410 using a non-mechanical coupling or non-mechanical mechanism (for example an electrical coupling). Typically, microtomes include a handwheel that is mechanically coupled to the motor. Such mechanical coupling, however, adds resistance to the handwheel when the user tries to turn it. Repeated turning of such a handwheel can be taxing on the user and may at times result in medical conditions such as carpal tunnel syndrome. The non-mechanical coupling or mechanism disclosed herein may offer the advantage of reduced handwheel resistance resulting in a handwheel that is easier to turn.

In some embodiments, the non-mechanical coupling or mechanism includes first encoder 461. First encoder 461 may be a rotary encoder coupled to shaft 462 of handwheel 404. Rotation of handwheel 404 and in turn shaft 462 provides first encoder 461 with an angular position of handwheel 404. First encoder 461 then converts the angular position to an electrical representation (for example an analog or digital code or value). This analog or digital code is transmitted to control circuit 418 via control line 419 where it is processed and used to direct movement of motor 410 and in turn feed drive 402. In some embodiments, motor 410 having feed drive 402 coupled thereto may be connected to control circuit 418 by second encoder 464. In this aspect, shaft 463 of motor 410 may be connected to second encoder 464 so that second encoder 464 may detect a position of motor 410 during the cutting operation. Encoder 464 then converts this position information to an electrical representation (for example an analog or digital code or value) and transmits the electrical representation to control circuit 418 via control line 420. In some embodiments, control circuit 418 may control the motor based at least in part on the electrical representation of the angular position of the handwheel. For example, since positions of both handwheel 404 and motor 410 are known, control circuit 418 can ensure that the position of handwheel 404 corresponds to, and is in alignment with, the position of motor 410 during a cutting operation. For example, rotation of handwheel 404 may not cause movement of motor 410 until a comparison of signals from the respective first and second encoders indicate that a position of handwheel 404 is aligned with a position of drive shaft of motor 410. This may tend to increase safety of operation of the microtome, especially when transferring from an automated mode of sectioning to a manual mode of sectioning. Motor 410 may be a single motor or may represent more than one motor, operable as previously discussed to drive, for example, vertical and/or horizontal movement of the microtome feed drive system.

Control device 416 may further be operable to initiate an automated cutting operation. Control device 416 may be any type of input device suitable for initiating a cutting operation. Representatively, control device 416 may include, for example, a keyboard, a keypad, a capacitive sensor touch pad, or other user data input device. In some embodiments, signals are transmitted between control device 416 and control circuit 418 via control line 423. In other embodiments, control device 416 may be a wireless control device that is operable to transmit wireless control signals to control circuit 418 and optionally receive wireless signals from control circuit 418. The control line 423 may be omitted. Wireless control device 416 may have a wireless transmitter, wireless receiver, and/or wireless transceiver, a wireless protocol stack, and other conventional components found in wireless devices. In one aspect, wireless control device 416 may be a Bluetooth capable device, although this is not required.

Control device 416 may include keys or simulated keys that can be used to control the actions of the microtome. Representatively, the keys may present graphic symbols or text corresponding to the various operations of the microtome, such as arrows corresponding to a vertical or horizontal movement of the microtome and/or other words, symbols, pictures, or the like, corresponding to, for example, slicing, stop, start, trim a bottom of a cassette, section, locking, or other microtome operations. The user selects the operation to be performed using the control device 416 and pushes the appropriate key(s) to initiate the desired operation. The control signal is transmitted from control device 416 to control circuit 418. Control circuit 418 then provides a signal to, for example, motor 410 to initiate a cutting operation. The cutting operation may then continue automatically or autonomously substantially without additional user intervention until the user either presses a stop key or a preprogrammed cutting operation is completed. The cutting operation may also be stopped by the operator pressing on a foot switch without using his/her hands.

Sample holders capable of realigning an orientation of a surface of a sample so that they are parallel or more parallel with a cutting member and/or a cutting plane are known in the arts. In some embodiments, the feed drive system may have a multi-axis workpiece chuck or motorized chuck that is capable of adjusting an orientation of the cutting surface of the sample in two dimensions relative to a cutting member and/or cutting plane. Examples of suitable multi-axis workpiece chucks are described in U.S. Pat. No. 7,168,694, entitled "MULTI-AXIS WORKPIECE CHUCK," by Xuan S. Bui et al., filed on Jan. 22, 2004, and assigned to the assignee of the present application. In one embodiment, the multi-axis chuck may have a mounting assembly that retains a workpiece, such as a sample, in a substantially fixed orientation with respect to the chuck. The chuck may be motor-driven and may be rotatable about at least two axes which may be perpendicular. The chuck may be rotated manually by an operator using a controller that is in communication with one or more motors, or the microtome may autonomously rotate the chuck. One or more sensors may be used to sense a position of the chuck. According to one embodiment, each axis may have three sensors that detect a middle nominal position and end positions of the chuck. A user or the microtome may control movement of the chuck by signaling the motor to rotate the chuck to the desired position. The sensors may be used to determine whether the desired position has been reached. In one embodiment, the chuck may include first and second portions that are rotatable about at least two orthogonal axes. The first portion may rotate about a first axis and independently of the second portion. Rotation of the second portion about a second axis may cause the first portion to rotate about the second axis also. This may allow the chuck to be rotatable in multiple dimensions.

In some embodiments, a locking mechanism may also optionally be provided. After rotating the multi-axis chuck, a locking mechanism may be engaged to lock the multi-axis chuck in the desired position. This locking mechanism may be, for example, a permanent magnet solenoid, a geared motor or a rotating handle that causes the first, second, and third portions to lock by friction or other known manner. In one embodiment, a motor may be used to tighten the chuck at times when the chuck is not being adjusted. When the microtome determines to adjust the position of the sample by adjusting the chuck, or when a user decides to manually adjust the position of the tissue sample by adjusting the chuck, the motor may be signaled to loosen the chuck to allow the chuck to be adjusted. At other times, when the position of the chuck is not being adjusted, the motor may be signaled to maintain the chuck in a tightened or locked configuration so that the position of the chuck and/or the position of a sample held by the chuck do not change unintentionally.

Returning to FIG. 1, in some embodiments, a sectioning cycle may include: (1) moving sample block 108 in a forward horizontal direction toward the cutting plane a predetermined distance related to the desired slice thickness; (2) moving sample block 108 in a vertical direction (for example downward) toward the cutting member to obtain a slice; (3) moving the sample block 108 in a backward or opposite horizontal direction away from the cutting plane and/or cutting member a predetermined distance; and (4) moving sample block 108 in an opposite vertical direction (for example upward) away from the cutting member. Retracting or moving the sample block 108 in a backward horizontal direction away from the cutting member helps to avoid sample block 108 contacting the cutting member during (4) when moving sample block 108 in the opposite vertical direction (for example upward) away from the cutting member. Representatively, the distance sample block 108 is retracted may correspond to a thickness of the sliced sample. Alternatively, it is contemplated that in some embodiments, the retraction step may be omitted. The slicing cycle may be repeated until a desired number of slices are obtained.

In the foregoing specification, the invention has been described with reference to specific embodiments thereof. It will, however, be evident that various modifications and changes can be made thereto without departing from the broader spirit and scope of the invention as set forth in the appended claims. The specification and drawings are, accordingly, to be regarded in an illustrative rather than a restrictive sense.

In the description above, for the purposes of explanation, numerous specific details have been set forth in order to provide a thorough understanding of the embodiments of the invention. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known circuits, structures, devices, and operations have been shown in block diagram form or without detail in order to avoid obscuring the understanding of the description.

It will also be appreciated, by one skilled in the art, that modifications may be made to the embodiments disclosed herein, such as, for example, to the sizes, shapes, configurations, couplings, forms, functions, materials, and manner of operation, and assembly and use, of the components of the embodiments. All equivalent relationships to those illustrated in the drawings and described in the specification are encompassed within embodiments of the invention. Further, where considered appropriate, reference numerals or terminal portions of reference numerals have been repeated among the figures to indicate corresponding or analogous elements, which may optionally have similar characteristics.

Various operations and methods have been described. Some of the methods have been described in a basic form, but operations may optionally be added to and/or removed from the methods. In addition, while a particular order of the operations according to example embodiments has been described, it is to be understood that that particular order is exemplary. Alternate embodiments may optionally perform the operations in different order, combine certain operations, overlap certain operations, etc. Many modifications and adaptations may be made to the methods and are contemplated.

One or more embodiments include an article of manufacture (e.g., a computer program product) that includes a machine-accessible and/or machine-readable medium. The medium may include, a mechanism that provides (e.g., stores) information in a form that is accessible and/or readable by the machine. The machine-accessible and/or machine-readable medium may provide, or have stored thereon, a sequence of instructions and/or data structures that if executed by a machine causes or results in the machine performing, and/or causes the machine to perform, one or more or a portion of the operations or methods disclosed herein. In one embodiment, the machine-readable medium may include a tangible non-transitory machine-readable storage media. For example, the tangible non-transitory machine-readable storage media may include a floppy diskette, an optical storage medium, an optical disk, a CD-ROM, a magnetic disk, a magneto-optical disk, a read only memory (ROM), a programmable ROM (PROM), an erasable-and-programmable ROM (EPROM), an electrically-erasable-and-programmable ROM (EEPROM), a random access memory (RAM), a static-RAM (SRAM), a dynamic-RAM (DRAM), a Flash memory, a phase-change memory, or a combinations thereof. The tangible medium may include one or more solid or tangible physical materials, such as, for example, a semiconductor material, a phase change material, a magnetic material, etc.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:
1. A sample sectioning device comprising:
   a cutting mechanism that is operable to cut sections from a sample;
   a sample holder that is operable to hold the sample;
   a drive system coupled with the sample holder to drive movement of the sample holder; and
   a rotating member coupled to the drive system to drive movement of the drive system, the rotating member having a reciprocating arm operable to rotate 180 degrees between a first vertical position and a second vertical position.

2. The sample sectioning device of claim 1 wherein the rotating member further comprises a vertically oriented rotating disk member attached to the reciprocating arm.

3. The sample sectioning device of claim 1 wherein the reciprocating arm rotates between the first vertical position that aligns the sample holder with the cutting mechanism and the second vertical position that aligns the sample holder with a surface orientation sensor.

4. The sample sectioning device of claim 1 wherein movement of the reciprocating arm along an angle of rotation between 0 degrees and 90 degrees produces a slicing movement of the sample holder.

5. The sample sectioning device of claim 1, further comprising logic to allow a configurable sectioning length to be specified, wherein the rotating member is to move the sample at a relatively slower speed of movement during the specified sectioning length and at a relatively faster speed of movement during at least one of just before and just after the movement during the specified sectioning length.

6. The sample sectioning device of claim 5, wherein the logic comprises logic to allow an operator to select the sectioning length from among a plurality of predetermined sectioning lengths each corresponding to a different type of cassette used to hold the sample.

7. The sample sectioning device of claim 5, wherein the logic comprises logic to allow an operator to specify the sectioning length by selecting one of a plurality of different types of cassettes.

8. The sample sectioning device of claim 1 further comprising:
a handwheel;
a first encoder coupled with the handwheel by a first shaft, the first encoder operable to generate an electrical representation of an angular position of the handwheel;
a motor of the drive system;
a second encoder coupled with the motor of the drive system by a second shaft, the second encoder operable to generate an electrical representation of an angular position of the motor of the drive system; and
a control circuit electrically coupled with the first and second encoders and operable to receive the electrical representations of the angular positions of the handwheel and the motor, the control circuit operable to control the motor based at least in part on the electrical representation of the angular position of the handwheel.

* * * * *